United States Patent [19]
Kubo et al.

[11] Patent Number: 5,997,874
[45] Date of Patent: Dec. 7, 1999

[54] DIHYDROPHENANTHRENE

[75] Inventors: Michinori Kubo, Sakai; Masayuki Yoshikawa, Minoo; Hideaki Matsuda, Habikino; Hisashi Matsuda; Toshiyuki Murakami, both of Kyoto; Hiromi Shimada, Toyonaka; Tetsuo Sakurama, Osaka; Manabu Nomura, Miyazaki-gun, all of Japan

[73] Assignee: Nomura Co., Ltd., Miyazaki, Japan

[21] Appl. No.: 09/030,730

[22] Filed: Feb. 25, 1998

Related U.S. Application Data

[62] Continuation-in-part of application No. 08/661,970, Jun. 12, 1996, Pat. No. 5,750,107, which is a continuation-in-part of application No. 08/167,828, filed as application No. PCT/JP93/00187, Feb. 17, 1992, abandoned.

[30] Foreign Application Priority Data

Mar. 25, 1997 [JP] Japan ..................................... 9-113304
Mar. 25, 1997 [JP] Japan ..................................... 9-113305

[51] Int. Cl.$^6$ .......................... A01N 65/00; A01N 31/00; A01N 31/14; A01N 33/18; A01N 29/02; C07C 211/00

[52] U.S. Cl. ...................... 424/195.1; 514/712; 514/717; 514/742; 514/757; 564/308

[58] Field of Search .......................... 424/195.1; 514/706, 514/712, 715, 716, 717, 732, 738, 741, 742, 753, 757; 564/308, 377, 631, 747

[56] References Cited

U.S. PATENT DOCUMENTS 3,971,651  7/1976  Hashimoto et al. ..................... 504/348

OTHER PUBLICATIONS

Letcher et al. Chemical Constituents of the Combretaceae. Part. I. Substituted Phenanthrenes and 9,10–Dihydrophenenthrenes from the Heartwood of Combretum apiculatum. J. Chem. Soc. (C) (1971) p. 3070–3076.

Letcher et al. Chemical Constituents of the Combretaceae. Part. II. Substituted Phenanthrenes and 9,10–Dihydrophenenthrenes from the Heartwood of Combretum molle. J. C. S. Perkin I (1972) p. 206–210.

Carvalho et al. "Boron Trichloride as a Selective Demethylating Agent for Hindered Ethers," J. Chem. Soc., Chem. Commun. (1984) p. 227–229.

*Primary Examiner*—Jon P. Weber
*Assistant Examiner*—Susan Hanley
*Attorney, Agent, or Firm*—Sheridan Ross P.C.

[57] ABSTRACT

The present invention relates to a class of dihydrophenanthrene which are isolated from Calanthe discolor Lindl. and derivatives thereof.

16 Claims, No Drawings

DIHYDROPHENANTHRENE

CROSS REFERENCE TO RELATED APPLICATIONS

The present application is a continuation-in-part of U.S. patent application Ser. No. 08/661,970, filed Jun. 12, 1996, now U.S. Pat. No. 5,750,107, which is a continuation-in-part of U.S. patent Ser. No. 08/167,828 filed Dec. 16, 1993, now abandoned, which is a United States national phase application based on PCT/JP93/00187, which has a priority date of Feb. 17, 1992. These applications are incorporated by reference herein in their entirety.

FIELD OF THE INVENTION

The present invention is related to a class of novel dihydrophenanthrene. More specifically, the present invention relates to a class of dihydrophenanthrene which are isolated from Calanthe discolor Lindl. and derivatives thereof.

BACKGROUND OF THE INVENTION

The alcohol extract from Calanthe discolor Lindl. is known to be useful for promotion of hair growth and restoration. (JP. A 5-294813) However, the components of this extract have not been identified.

Therefore, there is a need to isolate and identify the active components of the alcohol extract of Calanthe discolor Lindl. There also is a need for compounds that are derivatives of these active components which may be more active and possess other physiological activities.

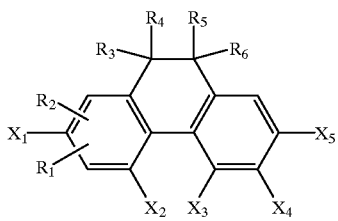

I wherein $X_1$, $X_2$, $X_3$, $X_4$, and $X_5$ are independently H, $OR_7$, $SR_8$, or $NR_9R_{10}$ to provided at least 3 of $X_1$, $X_2$, $X_3$, $X_4$, and $X_5$ are independently $OR_7$, $SR_8$ or $NR_9R_{10}$;

$R_1$, $R_2$, $R_3$, $R_4$, $R_5$, and $R_6$ are independently H, $OR_{11}$, $SR_{12}$, $NR_{13}R_{14}$, $C_1$–$C_4$ alkyl, or halogen; and $R_7$, $R_8$, $R_9$, $R_{10}$, $R_{11}$, $R_{12}$, $R_{13}$ and $R_{14}$ are independently H or $C_1$–$C_4$ alkyl.

One embodiment of the invention provides a compound 2,4-dimethoxy-3,5,7-trihydroxy-9,10-dihydrophenanthrene.

DETAILED DESCRIPTION OF THE INVENTION

The present invention is directed to a class of novel dihydrophenanthrenes.

More specifically, the present invention comprises a class of chemcial compounds isolated from Calanthe discolor Lindl. and derivatives thereof. The compounds of the present invention can be described by general formula I:

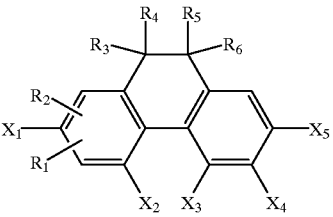

I $X_1$, $X_2$, $X_3$, $X_4$, and $X_5$ are independently H, $OR_7$, $SR_8$, or $NR_9R_{10}$. Preferably at least 3 of $X_1$, $X_2$, $X_3$, $X_4$, and $X_5$ are independently $OR_7$, $SR_8$ or $NR_9R_{10}$, more preferably at least 4 of $X_1$, $X_2$, $X_3$, $X_4$, and $X_5$ are independently $OR_7$, $SR_8$ or $NR_9R_{10}$, and most preferably $X_1$, $X_2$, $X_3$, $X_4$, and $X_5$ are independently $OR_7$, $SR_8$ or $NR_9R_{10}$. Preferably $X_1$ is $OR_{71}$ more preferably $X_1$ is OH. Preferably $X_2$ is $OR_7$, more preferably $X_2$ is OH. Preferably $X_3$ is $OR_7$, more preferably $X_3$ is $OCH_3$. Preferably $X_4$ is $OR_7$, more preferably $X_4$ is OH. Preferably $X_5$ is $OR_7$, more preferably $X_5$ is $OCH_3$.

$R_1$, $R_2$, $R_3$, $R_4$, $R_5$, and $R_6$ are independently H, $OR_{11}$, $SR_{12}$, $NR_{13}R_{14}$, $C_1$–$C_4$ alkyl, or halogen. Alkyl groups according to the invention are aliphatic hydrocarbons which can be straight or branched chain groups. Alkyl groups optionally can be substituted with one or more substituents, such as halogen, aryl, hydroxy, alkoxy, carboxy, oxo and cycloalkyl. There may be optionally inserted along the alkyl group one or more oxygen, sulfur or substituted or unsubstituted nitrogen atoms. Exemplary alkyl groups include methyl, ethyl, i-propyl, n-butyl, t-butyl, fluoromethyl, trifluoromethyl, chloromethyl, trichloromethyl, and pentafluoroethyl. Preferably at least two of $R_1$, $R_2$, $R_3$, $R_4$, $R_5$ and $R_6$ are H, still more preferably at least 4 of $R_1$, $R_2$, $R_3$, $R_4$, $R_5$ and $R_6$ are H, and most preferably $R_1$, $R_2$, $R_3$, $R_4$, $R_5$ and $R_6$ are H.

$R_7$, $R_8$, $R_9$, $R_{10}$, $R_{11}$, $R_{12}$, $R_{13}$ and $R_{14}$ are independently H or $C_1$–$C_4$ alkyl. Preferably $R_7$, $R_8$, $R_9$, $R_{10}$, $R_1$, $R_{12}$, $R_{13}$ and $R_{14}$ are independently H or methyl ($CH_3$).

Particularly preferred compounds of the present inventions include 2,4-dimethoxy-3,5 7-trihydroxy-9,10-dihydrophenanthrene.

The compounds of the present invention can be isolated from Calanthe discolor Lindl. For example, a method for preparing an extract from Calanthe discolor Lindl. and uses thereof as a hair growth promoter are disclosed in U.S. patent application Ser. Nos. 08/661,970 and 08/167,828. Alternatively, the compounds of the present invention can be synthesized from readily available starting materials.

Various substituents on the compounds of the present invention can be present in the starting compounds, added to any one of the intermediates or added after formation of the final products by known methods of substitution or conversion reactions. If the substituents themselves are reactive, then the substituents can themselves be protected according to the techniques known in the art. A variety of protecting groups are known in the art, and can be employed. Examples of many of the possible groups can be found in "Protective Groups in Organic Synthesis" by T. W. Green, John Wiley and Sons, 1981. For example, nitro groups can be added by nitration and the nitro group can be converted to other groups, such as amino by reduction, and halogen by diazotization of the amino group and replacement of the diazo group with halogen. Acyl groups can be added by Friedel-Crafts acylation. The acyl groups can then be transformed to the corresponding alkyl groups by various methods, including the Wolff-Kishner reduction and Clemmenson reduction.

Amino groups can be alkylated to form mono- and di-alkylamino groups; and mercapto and hydroxy groups can be alkylated to form corresponding ethers. Primary alcohols can be oxidized by oxidizing agents known in the art to form carboxylic acids or aldehydes, and secondary alcohols can be oxidized to form ketones. Thus, substitution or alteration reactions can be employed to provide a variety of substituents throughout the molecule of the starting material, intermediates, or the final product, including isolated products.

The compounds of the present invention have a variety of physiological properties including reducing the amount of smooth muscle contraction and causing relaxation of smooth muscles. Therefore, they can be used in a variety of application including as a vasodilator.

The compounds of the present invention can be administered to a patient to achieve a desired physiological effect. Preferably the patient is an animal, more preferably a mammal, and most preferably a human. The compound can be administered in a variety of forms adapted to the chosen route of administration, i.e., orally or parenterally. Parenteral administration in this respect includes administration by the following routes: intravenous; intramuscular; subcutaneous; intraocular; intrasynovial; transepithelially including transdermal, ophthalmic, sublingual and buccal; topically including ophthalmic, dermal, ocular, rectal and nasal inhalation via insufflation and aerosol; intraperitoneal; and rectal systemic.

The active compound can be orally administered, for example, with an inert diluent or with an assimilable edible carrier, or it can be enclosed in hard or soft shell gelatin capsules, or it can be compressed into tablets, or it can be incorporated directly with the food of the diet. For oral therapeutic administration, the active compound may be incorporated with excipient and used in the form of ingestible tablets, buccal tablets, troches, capsules, elixirs, suspensions, syrups, wafers, and the like. Such compositions and preparation can contain at least 0.1% of active compound. The percentage of the compositions and preparation can, of course, be varied and can conveniently be between about 1 to about 10% of the weight of the unit. The amount of active compound in such therapeutically useful compositions is such that a suitable dosage will be obtained. Preferred compositions or preparations according to the present invention are prepared such that an oral dosage unit form contains from about 1 to about 1000 mg of active compound.

The tablets, troches, pills, capsules and the like can also contain the following: a binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin can be added or a flavoring agent such as peppermint, oil of wintergreen, or cherry flavoring. When the dosage unit form is a capsule, it can contain, in addition to materials of the above type, a liquid carrier. Various other materials can be present as coatings or to otherwise modify the physical form of the dosage unit. For instance, tablets, pills, or capsules can be coated with shellac, sugar or both. A syrup or elixir can contain the active compound, sucrose as a sweetening agent, methyl and propylparabens a preservatives, a dye and flavoring such as cherry or orange flavor. Of course, any material used in preparing any dosage unit form should be pharmaceutically pure and substantially non-toxic in the amounts employed. In addition, the active compound can be incorporated into sustained-release preparations and formulation.

The active compound can also be administered parenterally. Solutions of the active compound as a free base or pharmacologically acceptable salt can be prepared in water suitably mixed with a surfactant such as hydroxypropylcellulose. Dispersion can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It can be stable under the conditions of manufacture and storage and must be preserved against the contaminating action of microorganisms such as bacterial and fungi. The carrier can be a solvent of dispersion medium containing, for example, water, ethanol, polyol (e.g., glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, e.g., sugars or sodium chloride. Prolonged absorption of the injectable compositions of agents delaying absorption, e.g., aluminum monostearate and gelatin.

Sterile injectable solutions are prepared by incorporating the active compound in the required amount in the appropriate solvent with various other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze drying technique which yield a powder of the active ingredient plus any additional desired ingredient from previously sterile-filtered solution thereof.

The therapeutic compounds of the present invention can be administered to a mammal alone or in combination with pharmaceutically acceptable carriers, as noted above, the proportion of which is determined by the solubility and chemical nature of the compound, chosen route of administration and standard pharmaceutical practice.

The physician will determine the dosage of the present therapeutic agents which will be most suitable for prophylaxis or treatment and it will vary with the form of administration and the particular compound chosen, and also, it will vary with the particular patient under treatment. The physician will generally wish to initiate treatment with small dosages by small increments until the optimum effect under the circumstances is reached. The therapeutic dosage can generally be from about 0.1 to about 1000 mg/day, and preferably from about 10 to about 100 mg/day, or from about 0.1 to about 50 mg/Kg of body weight per day and preferably from about 0.1 to about 20 mg/Kg of body weight per day and can be administered in several different dosage units. Higher dosages, on the order of about 2× to about 4×, may be required for oral administration.

EXAMPLES

Example 1

This example illustrates a method for isolating and characterizing 2,4-dimethoxy-3,5,7-trihydroxy-9,10-dihydrophenanthrene from Calanthe discolor Lindl.

Fresh rhizome (7.5 Kg) of Calanthe discolor Lindl. was cut into strips and extracted three times with hot MeOH (18 liter). The extracts were combined and concentrated to provide 330 g of methanol extract residue (4.4% yield). This methanol extract residue was extracted with ethyl acetate (EtOAc) and $H_2O$ (1:1). The aqueous layer was separated and concentrated to yield 225 g (3.0% overall yield) and was subjected to a reverse-phase silica gel chromatography (to remove sugars) with water-methanol as eluant to provide 13 g (1.7% overall yield) of a crude material. The crude material was further purified by silica gel column chromatography using the following eluant system: $CHCl_3$:MeOH (10:1 then 3:1 and then 1:1) followed by $CHCl_3$:MeOH:$H_2O$ (at 65:35:10(Lower Layer) then at 6:4:1) and finally MeOH. Of the eight fractions obtained, fraction 5 (4100 mg) was further purified by silica gel column chromatography using the following solvent system: $CHCl_3$:MeOH (at 20:1 then 10:1 then 5:1) and finally with MeOH. Of the seven resulting fractions, fraction 2 was further purified by a silica gel column chromatography using Hexane:EtOAc solvent system at 3:1 then at 1:1 and finally with EtOAc to provide 42.8 mg (0.00057% overall yield) of calanthenol as a light green non-crystal powder. High resolution FAB-MS (m/z): Calc. for $C_{16}H_{17}O_5(M+H)^+$: 289.1114, found: 289.1095. IR (KBr, $cm^{-1}$): 3446, 2854, 1508, 1082. UV (c=0.0006, $CHCl_3$, nm(log $\epsilon$)): 305(3.9), 275(4.0), 217(4.4). $^1H$ NMR ($CDCl_3$, 500 MHZ, $\delta$): 2.63 (4H, s), 3.75 (3H, s), 3.91 (3H, s), 6.40 (1H, d, J=2.6 Hz), 6.47 (1H, d, J=2.6 Hz), and 6.68 (1H, s). $^{13}C$ NMR ($CDCl_3$, 125 MHZ, $\delta$): 156.0, 154.7, 145.7, 142.1, 142.0, 137.2, 131.4, 119.2, 113.0, 108.0, 108.0, 104.3, 31.6, and 30.5. Positive-mode FAB-MS(m/z): 311 $(M+Na)^+$, 289 (M–H). Negative-mode FAB-MS (m/z) : 287 (M–H)

The peaks of pseudo molecular ion were observed at m/z 287 (M–H) by a negative mode FAB-MS and at m/z 311 $(M+Na)^+$ by a positive mode FAB-MS. The molecular formula of calanthenol was determined to be $C_{16}H_{16}O_5$ by a high resolution FAB-MS. IR spectrum of calanthenol showed a presence of a hydroxyl group (3446 $cm^{-1}$), an aromatic methoxy group (2854 $cm^{-1}$), an aromatic ring (1508 $cm^{-1}$) and an ether linkage (1082 $cm^{-1}$). The presence of two methoxy groups and two methylene groups was confirmed through 1H NMR and $^{13}C$ HCOSY NMR. Detailed analysis of two dimensional NMR ($^1H$—$^1H$, $^{13}C$-HCOSY) showed that calanthenol has 9,10-hydrophenanthrene skeleton with two methoxy groups and three hydroxy groups. The presence of two methoxy groups in the 2- and 4-positions of the phenanthrene ring moiety was determined by HMBC spectrum. A coupling between a proton in the 1-position and a methoxy group in the 2-position was observed in NEO different spectrum. Acetylation of calanthenol with acetic anhydride-pyridine resulted in incorporation of three acetyl groups indicating the presence of three hydroxy moieties. The chemical structure of calanthenol was determined to be 2 4-dimethoxy-3,5,7-trihydroxy-9,10-dihydrophenanthrene. The chemical structure of calanthenol (II) is shown below.

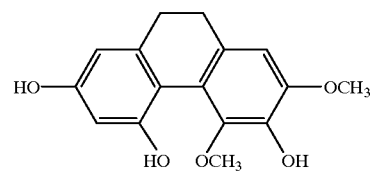

II

Example 2

This example illustrates derivatization of calanthenol.

Calanthenol was contacted with acetic anhydride-pyridine mixture to provide triacetyl calanthenol. The presence of three acetyl group was confirmed by $^1H$ NMR which showed three —$CH_3$ groups at $\delta$ 2.21 (3H, s), 2.29 (3H, s), and 2.36 (3H, s). The chemical structure of calanthenol triacetate (III) is shown below.

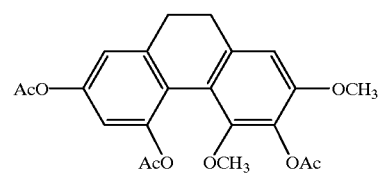

III

Example 3

Unless otherwise stated, dimethyl sulfoxide (DMSO) was used as the carrier solvent.

This example illustrates relaxation of muscles and inhibition of muscle contraction by calanthenol.

The experiment was conducted using thoracic aorta muscles from rats according to the procedure by Magnus. Briefly, the Magnus procedure involves placing a tissue in a Magnus appratus having a physiological solution such as Krebs Henseleit solution at about 37° C. with continuous introduction of gas, typically 95% oxygen and 5% carbon dioxide. One end of the tissue is attached to a fixed point of the Magnus apparatus and the other end of the tissue is attached to a force transducer which is used to measure the tension generated by the tissue. The force transducer can be connected to an amplifier and to a recording device such as a polygraph or a digital output device which provides a readily observable tension measurement.

Tension ($T_1$)of the muscle tissue was measured using a Magnus apparatus after addition of a test component, serotonin (5 to 10 M) and norepinephrine (6 to 10 M) to the muscle tissue. Tension ($T_0$) was measured using the same procedure without a test component. Percent muscle contraction inhibition is defined as:

% inhibition=$[1-(T_1/T_0)] \times 100$.

The results of the muscle contraction inhibition test are shown in Table 1.

The ability of calanthenol to cause muscle relaxation was also measured by the following experimental procedure.

Thoracic aorta muscle tissues from rats were placed on a Magnus apparatus and treated with 50 mM KCl solution and the tension of the tissue was measured ($T_0$) . A test component was added and the tension was again measured ($T'_1$). Percent muscle relaxation was calculated by the following formula:

% muscle relaxation=$[(T'_0-T'_1)/T'_0] \times 100$

The results of % muscle relaxation test are also shown in Table 1.

TABLE 1

| Test component | Concentration | % muscle contraction inhibition | | % muscle relaxation |
|---|---|---|---|---|
| | | serotonin | norepinephrine | KCl |
| Calanthenol | $10^{-4}$ M | 62 | 23 | 79 |
| MeOH extract | 50 µg/ml | 7 | 0 | 0 |
| EtOAc layer | 50 µg/ml | 30 | 0 | 24 |
| $H_2O$ layer | 50 µg/ml | 2 | 0 | 0 |
| Sugar eliminated MeOH extract | 50 µg/ml | 0 | 0 | 2 |
| DMSO | (control) | 0 | 0 | 0 |

As shown in Table 1, calanthenoL prevents muscle contraction and causes relaxation of muscles. Therefore, the novel class of dihydrophenanthrene compound of the present invention including calanthenol and derivatives thereof can be used as a vasodilator.

Those skilled in the art will appreciate that numerous changes and modifications may be made to the preferred embodiments of the invention and that such changes and modifications may be made without departing from the spirit of the invention. It is therefore intended that the appended claims cover all such equivalent variations as fall within the true spirit and scope of the invention.

What is claimed is:

1. A compound of the formula:

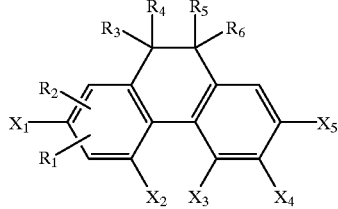

wherein
$X_1$, $X_2$, $X_3$, and $X_4$, are $OR_7$;
$X_5$ is H, $OR_7$, $SR_8$, or $NR_9R_{10}$;
$R_1$, $R_2$, $R_3$, $R_4$, $R_5$, and $R_6$ are independently H, $OR_{11}$, $SR_{12}$, $NR_{13}R_{14}$, $C_1$–$C_4$ alkyl, or halogen; and
$R_7$, $R_8$, $R_9$, $R_{10}$, $R_{11}$, $R_{12}$, $R_{13}$ and $R_{14}$ are independently H or $C_1$–$C_4$ alkyl.

2. The compound of claim 1, wherein $X_5$ is $OR_7$.
3. The compound of claim 2, wherein at least one $R_7$ is $C_1$–$C_4$ alkyl.
4. The compound of claim 1, wherein $X_1$ is OH.
5. The compound of claim 1, wherein $X_2$ is OH.
6. The compound of claim 1, wherein $X_4$ is OH.
7. The compound of claim 1, wherein $X_3$ is $OCH_3$.
8. The compound of claim 1, wherein $X_5$ is $OCH_3$.
9. The compound of claim 1, wherein $X_1$, $X_2$ and $X_4$ are OH.
10. The compound of claim 1, wherein $X_3$ and $X_5$ are $OCH_3$.
11. The compound of claim 1, wherein $X_1$, $X_2$ and $X_4$ are OH and $X_3$ and $X_5$ are $OCH_3$.
12. The compound of claim 11, wherein $R_1$, $R_2$, $R_3$, $R_4$, $R_5$, and $R_6$ are H.
13. A compound 2,4-dimethoxy-3,5,7-trihydroxy-9,10-dihydrophenanthrene.
14. A composition, comprising:
 (a) a compound of the formula:

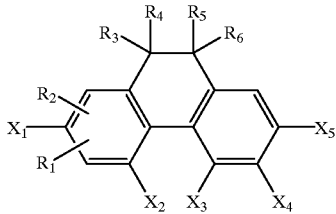

wherein
$X_1$, $X_2$, $X_3$, $X_4$, and $X_5$ are independently H, $OR_7$, $SR_8$, or $NR_9R_{10}$, provided at least 3 of $X_1$, $X_2$, $X_3$, $X_4$, and $X_5$ are independently $OR_7$, $SR_8$ or $NR_9R_{10}$;
$R_1$, $R_2$, $R_3$, $R_4$, $R_5$, and $R_6$ are independently H, $OR_{11}$, $SR_{12}$, $NR_{13}R_{14}$, $C_1$–$C_4$ alkyl, or halogen; and
$R_7$, $R_8$, $R_9$, $R_{10}$, $R_{11}$, $R_{12}$, $R_{13}$ and $R_{14}$ are independently H or $C_1$–$C_4$ alkyl; and
 (b) a pharmaceutically acceptable carrier.
15. The composition of claim 14, wherein said composition is formulated for parenteral administration.
16. The composition of claim 14, wherein said composition is formulated for oral administration.

* * * * *

UNITED STATES PATENT AND TRADEMARK OFFICE
CERTIFICATE OF CORRECTION

PATENT NO. : 5,997,874
DATED : December 7, 1999
INVENTOR(S) : Kubo et al.

It is certified that error appears in the above-identified patent and that said Letters Patent is hereby corrected as shown below:

On Column 1, line 35 please add the following:

SUMMARY OF THE INVENTION

The present invention provides a compound of the formula:

Signed and Sealed this

Nineteenth Day of September, 2000

Attest:

Q. TODD DICKINSON

*Attesting Officer*     *Director of Patents and Trademarks*